United States Patent [19]
Walker

[11] Patent Number: 5,322,513
[45] Date of Patent: * Jun. 21, 1994

[54] EASY-TO-HANDLE, SELF-GUIDING CATHETER STRIPPER

[75] Inventor: Blair D. Walker, Long Beach, Calif.

[73] Assignee: Baxter International Inc., Deerfield, Ill.

[*] Notice: The portion of the term of this patent subsequent to Nov. 16, 2010 has been disclaimed.

[21] Appl. No.: 89,352

[22] Filed: Jul. 9, 1993

Related U.S. Application Data

[63] Continuation of Ser. No. 823,926, Jan. 22, 1992, Pat. No. 5,261,887.

[51] Int. Cl.$^5$ .............................. A61M 5/00
[52] U.S. Cl. .................... 604/161; 604/264
[58] Field of Search .............. 604/158, 161, 162, 164, 604/171, 264, 280, 96; 128/656–658; 30/329

[56] References Cited

U.S. PATENT DOCUMENTS

| | | | |
|---|---|---|---|
| 2,109,108 | 2/1938 | Fesler . | |
| 3,624,901 | 12/1971 | Petit et al. . | |
| 4,166,469 | 9/1979 | Littleford . | |
| 4,306,562 | 12/1981 | Osborne | 604/280 |
| 4,394,828 | 7/1983 | Garbis et al. . | |
| 4,581,025 | 4/1986 | Timmermans | 604/264 |
| 4,631,059 | 12/1986 | Wolvek et al. | 604/280 |
| 4,687,469 | 8/1987 | Osypka | 604/161 |
| 4,748,982 | 6/1988 | Horzewski et al. . | |
| 4,762,129 | 8/1988 | Bonzel . | |
| 4,870,757 | 10/1989 | Kirkpatrick et al. | 30/344 |
| 4,988,356 | 1/1991 | Crittenden et al. . | |
| 4,997,424 | 3/1991 | Little | 604/280 |
| 5,058,273 | 10/1991 | Streger | 30/164.9 |
| 5,104,388 | 4/1992 | Quackenbush | 604/264 |
| 5,140,751 | 8/1992 | Faust | 30/91.1 |
| 5,188,606 | 2/1993 | Maloney et al. | 604/161 |

FOREIGN PATENT DOCUMENTS

| | | |
|---|---|---|
| 2607 | 6/1979 | European Pat. Off. . |
| 162982 | 12/1985 | European Pat. Off. . |
| 238018 | 9/1987 | European Pat. Off. . |
| A10371486 | 6/1990 | European Pat. Off. . |
| 391544 | 10/1990 | European Pat. Off. . |
| 402057 | 12/1990 | European Pat. Off. . |
| 416734 | 3/1991 | European Pat. Off. . |
| 486157 | 5/1992 | European Pat. Off. . |
| 3420455 | 5/1985 | Fed. Rep. of Germany . |
| WO9101156 | 2/1991 | PCT Int'l Appl. . |
| WO92/08510 | 5/1992 | PCT Int'l Appl. . |

*Primary Examiner*—Randall L. Green
*Assistant Examiner*—Mary Beth O. Jones
*Attorney, Agent, or Firm*—Debra D. Condino; Raymond Sun

[57] ABSTRACT

An integrated catheter stripper is mounted within a modified Y-connector that is used to seal a catheter on a guide wire. The connector is provided with a stripping port that opens into the central bore of the main body of the connector. A catheter slitter is mounted over the guide wire within the central bore of the main body for slitting the catheter as the catheter slides in the proximal direction along the guide wire within the main body. The split catheter is removed through the stripping port, which can be sealed during an angioplasty operation when the catheter is in use.

In non-integrated embodiments of the invention the catheter stripper is separate from the Y-connector and has a main body, a blade mounted in the main body, and an arrangement for aligning the catheter with the blade and for permitting mounting and separation of the blade relative to the catheter only by substantially longitudinal movement. In one embodiment, a styler is securely attached to the main body portion and extends into the proximal end of the catheter as it is pulled from the guide wire. In another embodiment, a guide tube, rather than a stylet, is secured to the main body and encircles the guide wire. The guide tube is pushed into the proximal end of the catheter (while the catheter is still on the guide wire) and a blade slits the catheter.

3 Claims, 3 Drawing Sheets

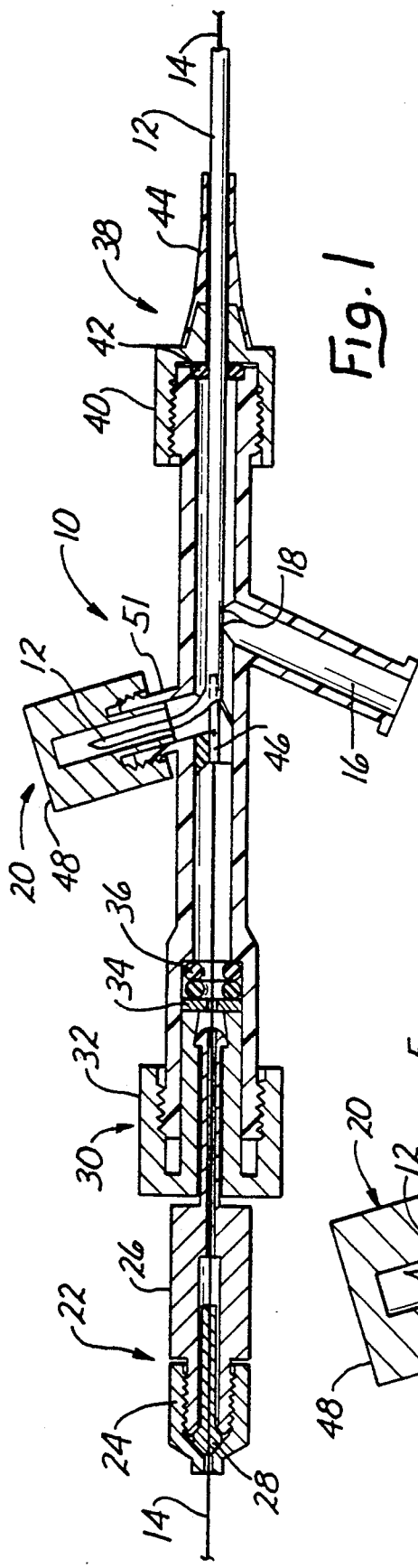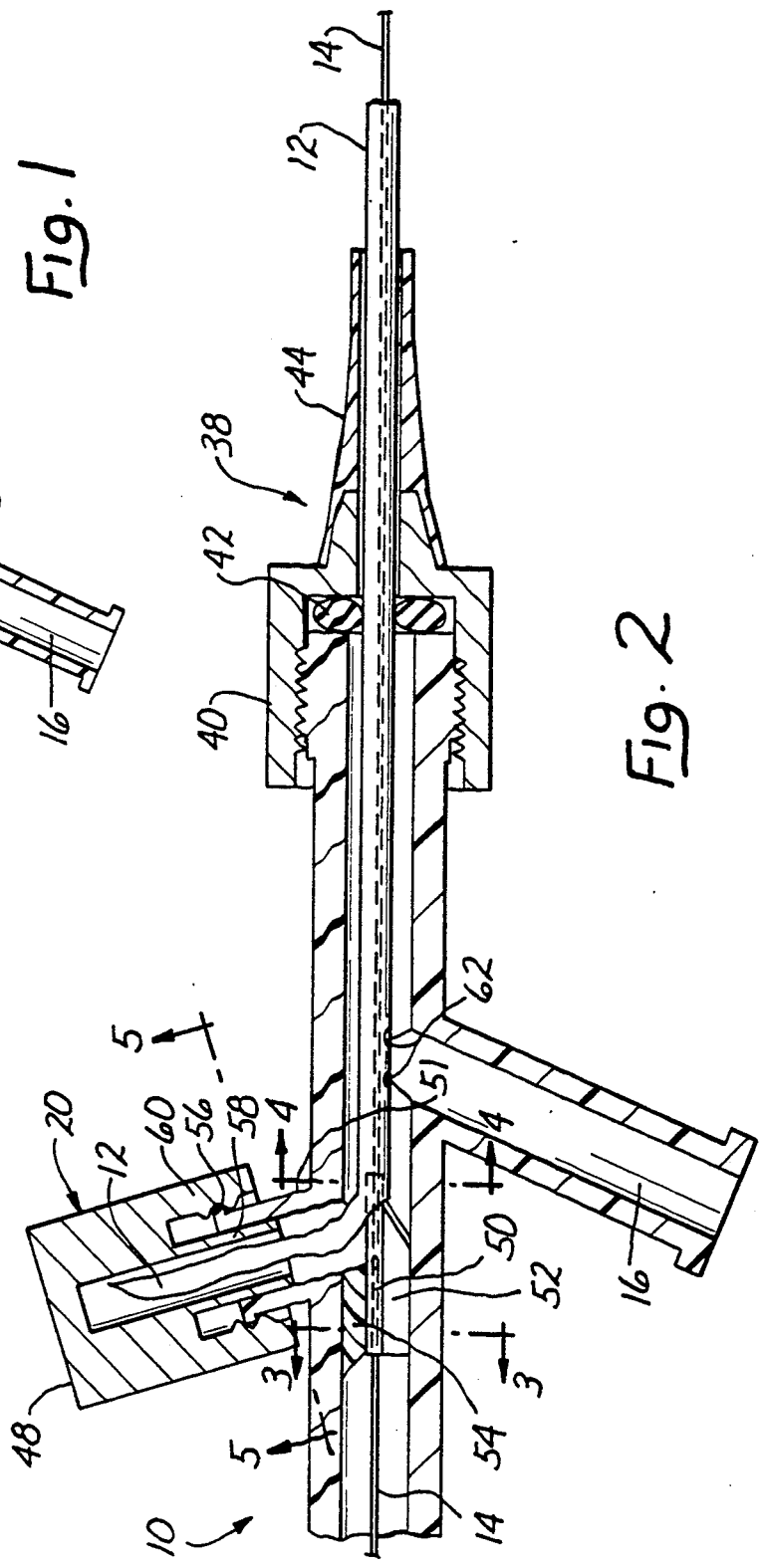

EASY-TO-HANDLE, SELF-GUIDING CATHETER STRIPPER

This application is a continuation of U.S. application Ser. No. 07/823,926 filed on Jan. 22, 1992, now U.S. Pat. No. 5,261,887.

FIELD OF THE INVENTION

The present invention relates to apparatus and associated methods for rapidly and easily removing catheters, particularly dilatation catheters, from guide or support wires, even when the wires remain within the body of a patient.

BACKGROUND OF THE INVENTION

Safety, precision and speed are essential to successful medical procedures. Furthermore, the less invasive a medical procedure is, the greater are the prospects that the patient will recover quickly and without complications. For example, because of its success and relatively low level of invasiveness, the medical procedure known as angioplasty has become a widely accepted method for opening obstructions ("stenoses"). throughout the vascular system, particularly in the coronary arteries. The most common form of angioplasty practiced to date is known as percutaneous transluminal coronary angioplasty (PTCA).

In virtually all forms of PTCA, a dilatation catheter having an inflatable balloon at its distal end is guided into a patient's artery and maneuvered within the artery until the balloon is positioned across the narrowing stenosis responsible for inadequate blood flow to the heart. The balloon is then inflated for a brief period, usually for no more than a few minutes, in order to displace or remodel the plaque or other obstruction causing narrowing in the artery. The deflated catheter is withdrawn when the stenosis has been opened and blood is once again flowing adequately. Thus, in contrast to the serious risks and complications previously associated with open-heart surgery, PTCA can be utilized to open blocked coronary arteries using only a small vascular incision through which the dilatation catheter is inserted and operated.

In most forms of angioplasty the dilatation catheter is guided into position through the patient's arteries using a flexible guide wire of very small diameter. Typically, guide wires are formed of surgical grade stainless steel with a diameter on the order of 0.25-0.46 mm (0.010 to 0.018 inches) and an overall length of approximately 175 cm. The distal end of the guide wire, that is, the end that enters the patient and is farthest away from the physician, is typically extremely flexible and may be formed as a coil of very small diameter wire. The end may also be slightly curved in order to make it easier for the physician to maneuver the guide wire around and through bends and junctions in the artery as the arterial pathway is particularly convoluted and branched near the heart.

Once the guide wire is positioned across the target lesion, that is, the site of the stenosis, an appropriately sized dilatation catheter is slid, or "advanced" over the guide wire (hence the- common designation of this arrangement as "over-the-wire"). At this point in the procedure the dilatation balloon, which is a portion of the catheter, is deflated and has a minimal cross-sectional diameter; this in turn makes it easier to position the balloon across the lesion before inflation. At various times throughout the procedure, radiopaque dyes are injected into the artery so that the cardiac physician, by watching a fluoroscope, can see the catheter's position in the artery, and can know when the balloon is properly in place.

One difficulty that may be associated with "over-the-wire" dilatation catheters is that unless the catheter and guide wire are positioned simultaneously the guide wire is positioned across the lesion before the catheter. In order to control the catheter the guide wire must extend outside the patient's body far enough to enable the catheter to be threaded along the wire without disturbing the positioning of the guide wire across the lesion. Similarly, if it becomes necessary to exchange or replace the dilatation catheter with a second catheter or device it is equally desirable to retain control of the guide wire access across the lesion.

The most obvious way to address these problems is to increase the length of the guide wire to ensure that a sufficiently long portion of the guide wire extends outside the patient's body. This can be accomplished in two ways. First, a guide wire extension may be "docked" or joined to the proximal end of the guide wire (the end closest to the physician) extending outside of the patient. Because the average dilatation catheter ranges from 120 cm to 160 cm in length, the guide wire extension must be of comparable length. As a result, the guide wire extension is awkward to handle and manipulate. Additionally, following positioning or exchange of the catheter the guide wire extension must be disconnected and moved out of the vascular physician's way. Further complicating matters, the junction between the proximal guide wire end and the docked extension may interfere with the smooth sliding of the catheter along the guide wire, decreasing the physician's control over the procedure.

Alternatively, an exceptionally long guide wire, on the order of 300 cm, can be used. This eliminates the problems associated with guide wire extensions and the additional docking and undocking steps. However, as with guide wire extensions the physician may need additional medical assistance just to monitor or manipulate the lengthy guide wire or may add the additional step of exchanging the long guide wire for a shortened wire following placement of the catheter.

A number of alternative dilatation catheter designs have been developed in an attempt to reduce or eliminate these problems. For example, "fixed-wire" dilatation catheters having a pre-positioned internal guide wire fixed to the catheter have-been used. These designs have proven quite maneuverable and relatively easy to position as the internal guide wire provides an additional degree of pushability and torqueability to the unitized device. However, to date such "fixed-wire" catheters have been unable to provide wire guided access to recross a lesion in the event of catheter failure or complications. Thus, even if it were possible to disconnect the catheter from the internal guide wire it would be necessary to utilize a lengthy guide wire or dock an exchange wire in order to retain guide wire access with such catheter designs.

Yet another alternative catheter design is the "monorail" variant of the over-the-wire system. Such a design is disclosed in U.S. Pat. No. 4,762,129 (Bonzel, Aug. 9, 1988). Catheters in a monorail system have two bores or "lumens." The balloon is inflated through one lumen and another, shorter, parallel lumen is threaded over the guide wire. This design enables the short, externally accessible monorail or guide wire lumen to be threaded over the proximal end of a pre-positioned guide wire without the need for docking a guide wire extension.

Regardless of the system, however, when a catheter must be removed from a guide wire, it should be possible to do so in a well-controlled manner quickly, easily, and safely without sacrificing the safety of guide wire access to the target lesion. It should also ideally be possible for a single physician to operate or remove the catheter without the need of an assistant.

More recent "rapid exchange" catheter designs directed to the elimination of unwieldy guide wire extensions have utilized a dedicated guide wire lumen provided with an overlapping longitudinal split seam. A specially designed proximal fitting is utilized to open this seam and direct the guide wire into the lumen as the catheter is advanced. This design enables the vascular physician to remove the catheter by simply grasping the proximal fitting and pulling the catheter off of the guide wire. An obvious drawback of this design is that it adds undesirable bulk to the catheter profile as well as undesirable complexity to the proximal fitting arrangement. Additionally, the split seam makes it possible to unintentionally remove the guide wire from the catheter.

Another possible method for stripping a catheter from a guide wire is simply for the physician to cut the catheter off with a scalpel or a knife as he (or an assistant) pulls it off the guide wire. This procedure is not as simple as it may appear. First, if the guide wire is to stay in position, this procedure usually requires an assistant. Second, quick removal of the catheter using a sharp, bare blade increases the risk that the physician will cut himself.

Along the lines, U.S. Pat. No. 4,997,424 (Little, et al., Mar. 5, 1991); U.S. Pat. No. 4,687,469 (Osypka, Aug. 18, 1987); and U.S. Pat. No. 4,631,059 (Wolvek et al., Dec. 23, 1986) all describe devices for cutting "introducers" from catheters. An introducer is a thin, tube-like device that is used to aid insertion of the surgical apparatus- such as a guide wire, with or without a catheter, into the artery or vein of a patient. The introducer is typically much stiffer than the distal end of a guide wire.

The guide wire, one will recall, is preferably as thin as possible, and its distal end is not suitable for pushing through the patient's skin, underlying muscular tissue, etc., and through the wall of the artery. Indeed, were the distal end sharp enough to do so, it might also be sharp enough to penetrate the wall of the artery as it is advanced within the artery toward the heart. Instead, an introducer is first pushed into the artery in order to provide an internal channel through which the guide wire can be fed. The catheter, assuming the assembly was not "fixed wire," can then be threaded over the guide wire within the introducer.

The devices described in the Little, Osypka and Wolvek patents all deal with the problem of removing the introducer once the various clamps, connectors, hubs, and other attachments are mounted on or around the guide wire and catheter. Using either the Little or the Osypka device, the physician lays a generally U-shaped channel of a guiding support portion on the surface of the catheter, so that a separating, forward edge fits between the outer surface of the catheter and, the inner surface of the introducer. The physician then pushes the device along the catheter, whereby an exposed blade slits the wall of the introducer to strip it away from the guide wire and catheter. The Wolvek device operates similarly, but it is a two-piece device that must be assembled around the introducer using a hinge.

These known devices are ill-suited for use in stripping a catheter from a guide wire. First, a physician attempting to use the Little and Osypka cutters would have to use great care to hold the channel-like supporting members against the long, thin, flexible guide wire while pulling the catheter with the other hand. Second, the exposed, presumably very sharp blades of these devices are a hazard to the physician and staff, especially during angioplasty operations where speed is essential. Third, each of these cutters is separate from the rest of the catheter/guide wire assembly, and thus represents yet another device that must be sterilized and kept track of separately in the operating room. Fourth, because the typical dilatation catheter is provided with a hard plastic Y-connector, it would be necessary to make the Y-connector removable because it would interfere with cutting the device.

The principal object of the invention is therefore to provide a device that enables a physician to strip catheters, even those with a uniform wall thickness, from a guide wire so quickly, easily and safely that it is well-suited for use during angioplasty operations. Another object is to avoid the disadvantages of guide wire extensions, docking, lengthly guide wires or an exposed blade when stripping the catheter from a guide wire.

SUMMARY OF THE INVENTION

According to an integrated embodiment of the invention, a catheter stripper is mounted within a modified Y-connector that is used to seal a balloon catheter on a guide wire. The connector is provided with a stripping port that opens into the central bore of the main body of the connector. A catheter slitter is mounted within the central bore of the main body for slitting the catheter as the catheter slides in the proximal direction along the guide wire within the main body. A sealing arrangement is also provided for sealing the stripping port opening when the connector is sealed, and for providing an opening through which the split catheter is drawn when the catheter is pulled proximally off of the guide wire.

In a preferred embodiment of the integrated catheter stripper according to the invention, the catheter stripper comprises a mounting tube that extends longitudinally and encircles the guide wire, and a blade secured to and extending radially from the mounting tube, with a cutting edge facing in the distal direction. The mounting tube preferably has a distal portion that extends in the distal direction farther than the blade, whereby the outer diameter of the mounting tube is less than the inner diameter of the catheter to permit the proximal end of the catheter to slide freely over the guide tube and against the cutting edge of the blade.

According to yet another aspect of the integrated embodiment of the invention, the catheter stripper includes a blade-stabilizing arrangement that is connected to the mounting tube and is in contact with the inner wall of the central bore of the connector for preventing longitudinal, transverse, and rotational movement of the blade relative to the stripping port.

In order to allow easy and quick access to the catheter as it is to be stripped from the guide wire, the stripping port preferably includes a mainly cylindrical access port that protrudes from the connector, and a removable cap that screws onto and seals the access port.

Non-integrated embodiments of the invention are also provided, in which the catheter stripper is separate from the Y-connector, but which avoid the risk of slipping inherent in existing designs. In these embodiments of the invention, the catheter stripper has a main body, a blade mounted in the main body, and an arrangement for aligning the catheter with the blade and for permitting mounting and separation of the blade relative to the catheter only by substantially longitudinal movement.

In one non-integrated embodiment, a stylet is securely attached to the main body portion and extends into the proximal end of the catheter as it is pulled from the guide wire. The stylet aligns the end of the catheter so that it contacts and is split by the blade as the catheter is pulled over the stylet.

In another preferred, non-integrated embodiment, a guide tube, rather than a stylet, is secured to the main body and encircles the guide wire. The guide-tube is pushed into the proximal end of the catheter (while the catheter is still on the guide wire) and a blade slits the catheter as the catheter is withdrawn over the guide wire. Alternatively, the stylet may be provided with an internal configuration that mates with the proximal end of the guide wire so that the blade and guide wire remain in position relative to one another as the catheter is withdrawn.

In both of the preferred, non-integrated embodiments of the invention, the main body of the catheter stripper has a protective shield portion that extends over the cutting edge of the blade to prevent the physician from being cut while stripping the catheter from the guide wire.

BRIEF DESCRIPTION OF THE DRAWINGS

FIG. 1 illustrates the main components of an arrangement for sealing and operating a guide wire and catheter, including a cross-sectional side view of an integrated embodiment of the catheter stripping arrangement according to the invention;

FIG. 2 is an enlarged view of the portion of FIG. 1 that includes a Y-connector in which the integrated catheter stripper is mounted;

DETAILED DESCRIPTION

Figure 3:
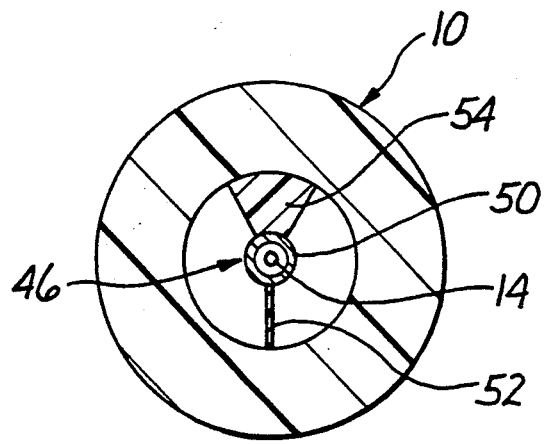
FIG. 3 is a cross-sectional view of the Y-connector taken along line 3—3 in FIG. 2, which also shows a preferred configuration for an integrated, catheter-slitting blade.

FIG. 1 shows generally an assembly used to hold and manipulate a guide wire and catheter during an angioplasty operation. In FIG. 1, a Y-connector is indicated generally by reference number 10. A catheter or body tube 12 is threaded over a guide wire 14 in a conventional manner. Beyond the far right portion of the arrangement shown in FIG. 1, it is assumed that the guide wire and catheter have been inserted into the body of a patient with the balloon portion (not shown) of the catheter in place across a lesion. Whereas the guide wire 14 typically will extend all the way through the assembly shown in FIG. 1, the end of the catheter 12 is led up into a stripping port 20, as is described in greater detail below.

In order to be able to inflate the balloon of the catheter 12, an inflation fluid, typically a contrast medium is pumped through an inflation port 16. This fluid enters the inside of the catheter through ports 18, that is holes, in the catheter 12 and around guide wire 14 where it exits body tube 12. It is therefore important to seal the assembly so that the inflation fluid does not leak out. The assembly shown in FIG. 1 illustrates a typical arrangement for sealing the guide wire and the catheter.

In this discussion, the common terms for orientation will be used. Accordingly, the "distal" end of the catheter, guide wire, or other part is the end farthest away from the physician who is maneuvering-the catheter. In FIG. 1, the distal end is therefore to the right. The "proximal" end is the end opposite the distal end, that is, the end closest to the operating physician. In FIG. 1, the proximal end is to the left.

At the far proximal end of the arrangement shown in FIG. 1 is a releasable end-tightening arrangement 22 in which a cap 24 screws onto a main body 26 and tightens down on a collet 28 around the guide wire 14. When tightened, collet 28 functions to retain the relative positioning of guide wire 14 within Y-connector 10. To the right of arrangement 22 in FIG. 1, the Y-connector 10 includes a further sealing arrangement 30, in which a cap 32 tightens down onto the proximal end of the Y-connector and, via a spacer 34, compresses guide wire seals 36. The guide wire seals 36 are preferably rubber O-rings and are shown in the unsealed position in FIG. 1. When the cap 32 is tightened down, the O-rings 36 will deform and seal tightly against the guide wire 14 and the inner walls of the Y-connector.

At its distal end, the Y-connector 10 has a distal sealing arrangement in which a compression hub 40 tightens down on the Y-connector and in doing so deforms at least one sealing O-ring 42 that then seals against the catheter 12 and the end of the Y-connector. In order to prevent the catheter 12 from kinking, the compression hub 40 preferably includes a strain relief member 44 that extends in the distal direction from the Y-connector.

The Y-connector is mainly tubular and, according to an integrated embodiment of the invention, a catheter slitter 46 is mounted over the guide wire 14 within the Y-connector 10. One end of the catheter 12 passes through an opening in the body of the Y-connector 10 into the stripping port 20. The stripping port 20 includes a sealing cap 48 which tightens onto and seals against a protruding access flange or port 51, which is preferably an integral part of the body of the Y-connector 10.

FIG. 2 shows the catheter stripper 46 and the stripping port 20 on a larger scale. The main parts of the catheter stripper 46 are a central tube 50, which is preferably of the type known in the industry as a hypo tube, a blade 52, and one or more supporting and stabilizing members 54. The tube 50 is substantially rigid and the guide wire 14 passes through the tube 50 within the Y-connector 10.

The blade 52 is attached along an upper edge of the hypo tube, with its sharpened surface shown angling away in the proximal direction. It is also contemplated as being within the scope of the invention to angle the sharpened surface away in the distal direction or, alternatively, to angle the sharpened surface orthogonally to the hypo tube. If the guide wire and catheter are viewed as defining an axis, the blade lies in a plane that extends radially from the axis. The blade may be attached by any conventional method such as by using soldering, brazing, welding, adhesives or mechanical locking. The outer edge of the blade 52 preferably conforms to the inner surface of the Y-connector 10. The blade 52 preferably extends from the central tube 50 on the opposite side of the tube from the stripping port 20. This ensures that the catheter, as it is being sliced, naturally and easily enters into the stripping port 20.

The preferred integrated embodiment of the invention includes at least one stabilizing member, which may be two stabilizing fins 54. Each fin 54 is attached along its central edge to the central tube 50. The outer edge of each fin preferably abuts the inner walls of the Y-connector 10. The blade 52 and the fins 54 thereby extend as planes radially outward from the central tube 50. As FIG. 2 shows, the stabilizing member extends only minimally, if at all, in the distal direction into the area under the access flange or port 51.

Instead of the fins 54, the central hypo tube 50 can be joined directly to the inner surface of the Y-connector 10 or by a single stabilizing member. This member would preferably be shaped as a section of a cylinder, and would thus take up the space delimited approximately by the fin 54 shown in FIG. 3. Regardless of the particular configuration used to join the catheter slitter 46 with the inside of the Y-connector 10, the joining member may either be permanently secured to the inside wall of the Y-connector, or the catheter slitter may be arranged to slide within the Y-connector and be locked in place using suitable grooves and latches. In the latter case, one or more guide grooves may be made in the inner wall of the Y-connector to guide the catheter slitter into position and suitable nibs may be provided to snap-lock the catheter slitter into position. The stripping port 20 is designed to allow the physician to strip the catheter 12 off of the guide wire quickly and easily, and also to make sure that the Y-connector 10 remains sealed when the stripping port is closed; thus, the catheter 12 can fill with the inflation liquid and its balloon will inflate properly. To this end, the access flange 51 that protrudes from the Y-connector 10 preferably includes an outward facing lip or threads 56 which interfaces with a cap 48 for closing port 20. In the preferred integrated embodiment of the invention, the cap 48 includes a central cylindrical collar 58 which fits snugly into the access port 51.

An outer annular portion 60 of the cap preferably includes threading that mates with the lip 56 of the access port 51. Instead of a single lip 56, the port 51 could of course be provided with conventional external threading that mates with the threading of the cap 48; sealing rings may also be provided between the cap 48 and the port 51.

As the cap 48 is screwed down onto the access port 51, the inner collar 58 bears against the inner surface of the port 51 and the threading bears against the lip 56. A seal is thereby created between the cap 48 and the access port 51 to prevent leakage of fluid from within the Y-connector 10. If even more positive sealing is required, O-rings or other conventional sealing members may be mounted either around the collar 58 or between the annular threaded portion of the cap 48 and the lip 56 or the outer surface of the access port 51. The inner collar 58 is preferrably hollow to allow the pre-stripped portion of the body tubing to extend past the end of port 51 while cap 48 is sealed. This will allow easy access for the physician to pull on the end of the body tubing once the cap 48 is removed.

During a typical angioplasty operation, the catheter 12 is threaded along the guide wire 14 until its balloon is in position or, alternatively, the catheter and guide wire may be releasably attached to one another and positioned within the patient as a unit. As those skilled in the art will appreciate, the majority of dilatation catheters are manufactured with Y-connector 10 sealingly positioned upon the proximal end of catheter 12. Thus, according to the invention, as the Y-connector is mounted onto the catheter and guide wire during manufacture, the most proximal end of the catheter 12 will run up against the catheter slitter 46. When the central tube 50 passes into the end of the catheter 12, it will begin to slit the underside (when viewed as in FIG. 2) of the catheter and the split end of the catheter is positioned in the stripping port 20 through the access port 51 that opens into the body of the Y-connector. Cap 48 is securely fastened onto the stripping port 20 so as to make a tight seal.

Thus, the apparatus of the present invention has little impact on the placement and operation of the dilatation catheter and may be adapted readily to existing single and multi-lumen catheter designs and procedures. Catheter placement and balloon inflation will take place in the normal manner as known in the art. It is only when it becomes necessary or desirable to remove the catheter from the patient's body that the distinct advantages of the present invention become manifest. At this time the present invention makes it possible to rapidly and easily remove the catheter while leaving the guide wire 14 in position across the target lesion. Rather than docking a guide wire extension or exchanging an extra long guide wire, according to the invention, the physician simply loosens cap 40 to release seal 42, unscrews the cap 48, and then pulls the catheter 12 away from the guide wire 14 and out through the stripping port 20. As the catheter 12 is pulled along the guide wire 14, the blade 52 will slit it underneath so that it will quickly "peel" upward through the stripping port 20. Tightened collet 28 secures guide wire 14 in position relative to Y-connector 10.

Following removal of all or the majority of catheter body 12 the Y-connector 10 can be removed from guide wire 14 by loosening collet 28 of tightening arrangement 22 and cap 32 of sealing arrangement 30. This releases the various attachments and seals about guide wire 14 and allows Y-connector 10 and any remaining portion of body 12 to be removed so that a replacement catheter or alternative apparatus may be threaded onto the proximal end of guide wire 14 and positioned within the patient's body.

FIG. 3 shows the Y-connector 10 and the catheter stripper 46 in cross section. As FIG. 3 shows, the blade 52 and the stabilizing fins or member 54 extend outward from the central tube 50 to bear against the inner cylindrical surface of the Y-connector 10.

Whereas the blade 52 is preferably made of highly-sharpened steel, the stabilizing and joining member 54 may be made of any suitable material that bonds well with the hypo tube 50 and that provides a smooth joint with the Y-connector.

Figure 4:
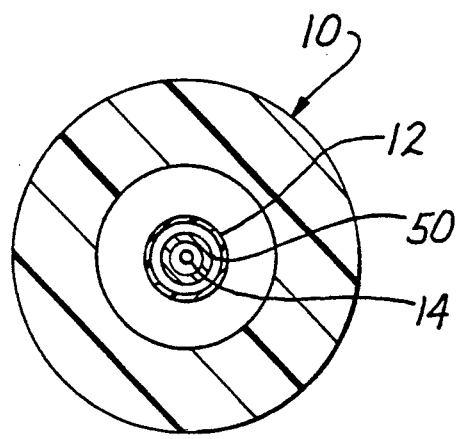
FIG. 4 is a cross-sectional view, taken along line 4—4 in FIG. 2, that shows how a supporting tube for the blade is mounted over a guide wire.

FIG. 4 shows a cross section of the Y-connector, catheter, catheter slitter and guide wire taken at a position before the catheter is split by the blade 52. As FIG.

4 shows, the diameter of the hypo tube 50 is preferably less than the inner diameter of the catheter. The hypo tube 50 preferably extends in the distal direction farther than the leading edge of the blade 52 so that the hypo tube can easily pass within the catheter and guide it against the blade.

Figure 5:
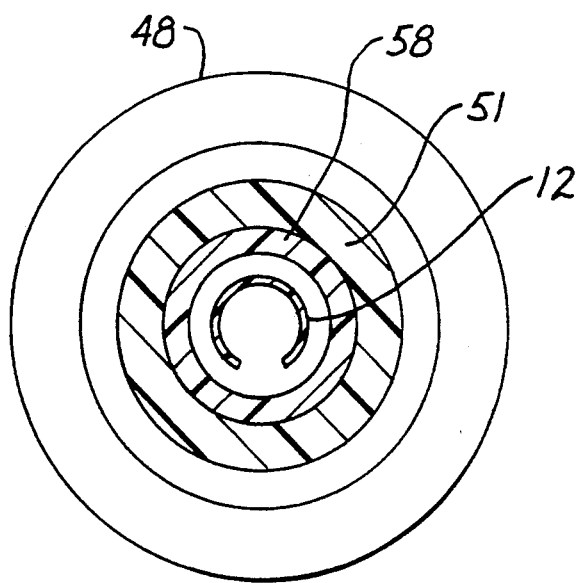
FIG. 5 is a cross-sectional view taken along line 5—5 in FIG. 2.

FIG. 5 shows a cross-section of the cylindrical access port 51 from the Y-connector 10, the inner collar 58 of the cap of the stripping port, and the split catheter 12. As FIG. 5 shows, there is preferably a sealing fit between the collar 58 and the inner wall of the access port 51. This figure also shows that the catheter is split after it passes the catheter stripper 46.

Figure 6:
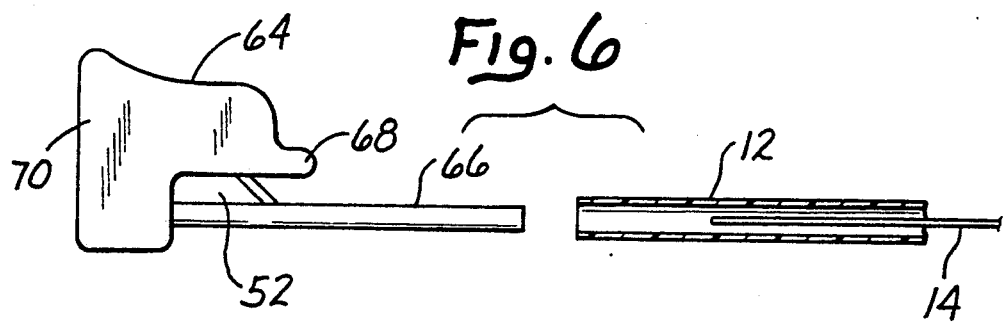
FIG. 6 illustrates a non-integrated, self-guiding embodiment of the catheter stripper according to the invention.

FIG. 6 illustrates a non-integrated embodiment of the catheter stripper according to the invention, which is suitable for removing a catheter from a guide wire in systems in which the Y-connector is first released from the tubing.

The non-integrated embodiment includes a holder 64, to which the blade 52 and a stylet 66 are attached. The holder 64 includes a main body portion 70 that the physician grasps, preferably between the thumb and index finger, as well as a protective shield portion 68, which extends over and beyond the blade in the direction of the stylet 66 to form a cutting gap between the shield portion and the stylet. The holder may be made of any metal or synthetic material that is rigid enough to hold the stylet and blade securely.

The blade 52 is angled so that its bottom edge (adjacent to the stylet) extends farther in the distal direction than its upper edge. The stylet 66 is substantially rigid and is secured in the main body portion 70 of the holder in a conventional manner; for example, it is preferably inserted securely into a receiving hole in the holder. An advantage of the stylet according to the invention is that it can be a simple thin rod with a circular cross section, and it is not necessary to manufacture it with a lengthwise groove that the physician must hold the guide wire in as he or she moves the catheter slitter along the guide wire. Indeed, using the stylet embodiment shown in FIG. 6, the catheter slitter does not even need to contact the guide wire, but rather the catheter is threaded onto the stylet and then pulled off of the guide wire as it is slit. The distal end of the stylet is preferably smoothed or rounded so that it will slide easily within the catheter and will not penetrate the catheter as the catheter is threaded onto the stylet.

The blade 52 may also be mounted in a suitable slot in the holder, or it may be attached in some other manner such as by welding or soldering (in the case of a metal holder), using adhesives, or mechanically. The blade is also attached to the stylet 66 using such conventional methods. When the holder is to be of molded plastic, the blade and stylet may be secured to each other to form a unit, onto which the holder is then molded. The holder is preferably unitary.

Figure 7:
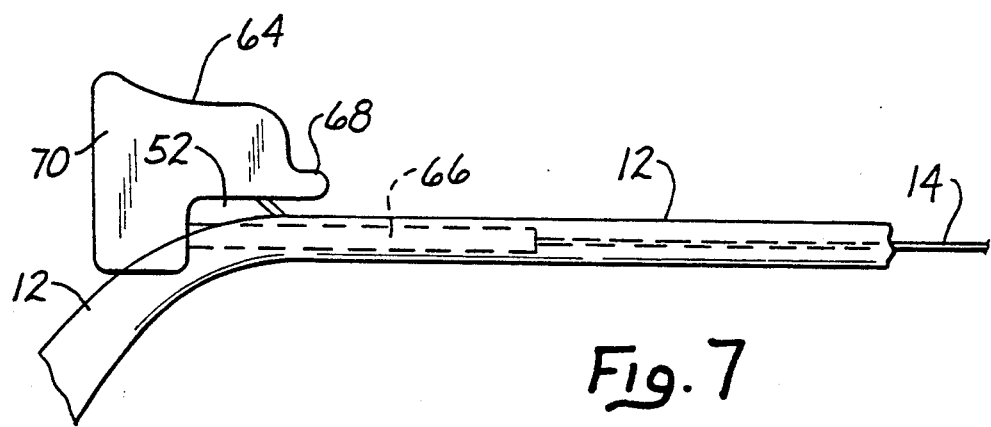
FIG. 7 illustrates the operation of the self-guiding embodiment shown in FIG. 6.

FIGS. 6 and 7 together illustrate the manner of use of the non-integrated embodiment of the invention. The Y-connector is first released so that the catheter is free to slide off of the guide wire. Holding the holder in one hand, the physician then inserts the stylet 66 into the free end of the catheter 12 and threads the catheter off of the guide wire by pulling the catheter toward the blade 52 with the other hand.

When the catheter reaches the blade, the blade will begin to slice it along its upper portion. By pulling the catheter outward and downward below the main body portion 64, the physician can quickly strip the catheter from the guide wire. One should note that the protective shield portion 68 prevents the blade from touching and cutting the physician's hand or finger, even when working quickly to remove the catheter so that another can be threaded onto the guide wire.

Furthermore, it is not necessary for the physician to concentrate on holding the catheter stripper against the surface of the catheter. Instead, once the stylet is inserted in the catheter, the stripper is self-guiding in that the catheter is held on the stylet until it is split, and the stylet ensures that the catheter is properly aligned and presented to the blade. The catheter cannot "jump" or "slip" off of the stylet as it is being stripped.

Figure 8:
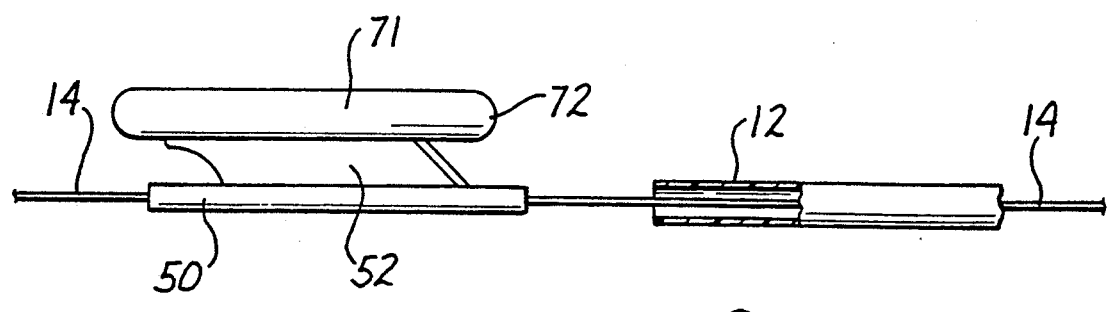
FIG. 8 illustrates an alternative embodiment of the non-integrated, self-guiding catheter stripper.

FIG. 8 illustrates an alternative, non-integrated embodiment of the catheter stripper according to the invention. Whereas, using the embodiment shown in FIGS. 6 and 7, the catheter slides off the proximal end of the guide wire and onto the stylet, in the alternative embodiment of FIG. 8, the catheter stripper itself is mounted on the guide wire.

The alternative, non-integrated embodiment includes a preferably unitary upper holding portion 71, with a distal, protective shield portion 72 that extends in the distal direction beyond the most distal point of the upward and backward angled blade 52 to form a cutting gap between the shield portion and the stylet. The material forming holding portion 71 and the attachment of the blade to the holding portion may be as described above for the non-integrated embodiment shown in FIGS. 6 and 7. Instead of a stylet, however, the alternative embodiment includes a guide tube 50, which is preferably a hypo tube.

The guide tube and blade are attached to each other as described above with reference to the integrated embodiment of the invention. The guide tube extends forward of the blade, and preferably forward of the most distal point of the shield portion 72.

To use the alternative embodiment, as before, the Y-connector is first released so that the catheter 12 is free to slide along the guide wire 14. The physician then slides the catheter stripper, in particular the guide tube 50, onto the guide wire (which can remain in place and need not be retracted). The physician then slides the catheter stripper along the guide wire until the distal end of the guide tube 50 enters the proximal end of the catheter 12. As the physician pulls the catheter off of the guide wire, it will pass over the distal end of the guide tube and will be guided toward and against the blade 52. The blade will thereby slit the catheter, which the physician can pull off downward and outward as in the embodiment shown in FIGS. 6 and 7 until the catheter is completely removed from the guidewire.

As before, the shield portion 72 prevents the blade from touching and cutting the physician's hand or finger, even when working quickly to remove one catheter so another can be threaded onto the guide wire. Also as before, it is not necessary for the physician to concentrate on holding the catheter stripper against the surface of the catheter or guide wire. Instead, once the guide tube is threaded onto the guide wire, the stripper is self-guiding, in that the catheter remains on the guide wire until it is split, and the guide tube ensures that the catheter is properly aligned and presented to the blade. The catheter stripper cannot "jump" or "slip" off of the guide wire as the catheter is stripped off of the wire, since the catheter stripper can be removed from the guide wire or catheter only by longitudinal motion—sliding it off of the end of the guide wire or out of the catheter.

Alternatively, guide tube 50 can be provided with a tapered internal bore narrowing toward its proximal end that will frictionally fit over the proximal end of guide wire 14. This configuration serves to securely position the apparatus on the guide wire and facilitates stripping of the catheter while retaining guide wire placement. Additionally, it is also contemplated as being within the scope of the present invention to provide the proximal end of guide wire 14 with a corresponding taper to facilitate this interlocking engagement of the guide wire and the catheter stripper. Alternatively, the guide wire above may be tapered to provide a friction fit. However, it should be emphasized that these features are not essential for the practice of the present invention but may be preferred for guide wire control.

There are many possible variations for the shape of the holding portions 70, 71. For example, instead of arranging a stylet 66 as in FIG. 6, one could mount the guide tube of FIG. 8 through the holder 64, so that the guide wire in the alternative, non-integrated embodiment would pass through the holder as well as through the guide tube.

It is also not necessary for the stripping port to have a protruding access port 51 with a mating cap 48. Instead, the stripping port could consist of a simple opening in the main body of the Y-connector, with a plug that screws into the opening, with a collar that slides over the opening, etc.

I claim:

1. A device for removing a catheter from a guide wire, in which the catheter has an inner diameter and a distal and a proximal end and extends mainly in a longitudinal direction when it is mounted on the guide wire and the guide wire has an outer diameter and a distal and a proximal end and extends mainly in a longitudinal direction, said device comprising:

a main body portion having a central bore;

means for slitting the catheter mounted and operably housed inside the central bore, the slitting means including a cutting edge; and means positioned inside the central bore for securing the position of the slitting means to prevent longitudinal, transverse and rotational movement of the slitting means relative to the main body portion.

2. The device of claim 1, further comprising a stripping port opening into the main body portion through which the catheter is drawn when the catheter is being slit by the slitting means when the catheter is moved proximally along the guide wire.

3. The device of claim 2, further comprising sealing means for sealing the stripping port.

* * * * *

UNITED STATES PATENT AND TRADEMARK OFFICE
CERTIFICATE OF CORRECTION

PATENT NO.    : 5,322,513
DATED         : June 21, 1994
INVENTOR(S)   : Blair D. Walker It is certified that error appears in the above-identified patent and that said Letters Patent is hereby corrected as shown below:

Title page,
Item [21], Application No., delete "89,352" and insert -- 08/089,352 --.
Item [63], Related U.S. Application Data, delete "Continuation" and insert -- Divisional --.

Column 1,
Line 5, delete "Continuation" and insert -- Divisional --.
Line 24, after "("stenoses")" delete "." (the period).

Column 2,
Line 50, delete "have-been" and insert -- have been --.

Column 8,
Line 34, delete "remove-the" and insert -- remove the --.
Line 38, delete "to-release" and insert -- to release --.

Signed and Sealed this

Twenty-eighth Day of December, 2004

JON W. DUDAS
*Director of the United States Patent and Trademark Office*